United States Patent [19]

Merlette

[11] Patent Number: 5,593,456
[45] Date of Patent: Jan. 14, 1997

[54] FOOT AND LEG PROSTHESIS AND METHOD OF MAKING SAME

[75] Inventor: John Merlette, Sandy, Utah

[73] Assignee: CRP, Inc., Salt Lake City, Utah

[21] Appl. No.: 243,989

[22] Filed: May 17, 1994

[51] Int. Cl.⁶ .................................................. A61F 2/66
[52] U.S. Cl. .......................... 623/49; 623/32; 623/55
[58] Field of Search ........................ 623/28, 32, 35, 623/42, 44, 46, 49, 52, 53, 55

[56] References Cited

U.S. PATENT DOCUMENTS

| | | | |
|---|---|---|---|
| 4,645,509 | 2/1987 | Poggi et al. | 623/55 |
| 4,822,363 | 4/1989 | Phillips | 623/27 |
| 4,959,073 | 9/1990 | Merlette | 623/55 |
| 4,994,086 | 2/1991 | Edwards | 623/26 |
| 5,037,444 | 8/1991 | Phillips | 623/55 |
| 5,062,859 | 11/1991 | Naeder | 623/55 |
| 5,156,631 | 10/1992 | Merlette | 623/52 |
| 5,156,632 | 10/1992 | Wellerhaus | 623/55 |
| 5,217,500 | 6/1993 | Phillips | 623/38 |
| 5,290,319 | 3/1994 | Phillips | 623/56 |

FOREIGN PATENT DOCUMENTS

| | | | |
|---|---|---|---|
| 2640499 | 6/1990 | France | 623/53 |
| 94019042 | 5/1994 | WIPO | 623/53 |

OTHER PUBLICATIONS

Springlite Gfott A Superior Sach Foot Alternative Pamphlet.
Photograph of actual Springlite G–Foot (labeled #1).
Photograph of Actual Springlite G–Foot (labeled #2).

*Primary Examiner*—Michael J. Milano
*Attorney, Agent, or Firm*—Workman, Nydegger & Seeley

[57] ABSTRACT

A foot prosthesis comprised of a single monolithic elongated composite member having a semi-flexible shank strut section, an ankle section, a forefoot section, and a toe section. One end of the shank strut section is connected to a socket which is adapted to receive an amputated leg stump. The other end smoothly curves downwardly, or downwardly and rearwardly, before curving forwardly of the shank strut section to the toe section. The invention is specially designed to accommodate lower limb amputee athletes participating in field and track events.

20 Claims, 3 Drawing Sheets

FOOT AND LEG PROSTHESIS AND METHOD OF MAKING SAME

BACKGROUND OF THE INVENTION

1. Field of the Invention

This invention relates to the field of lower leg and foot prostheses which attach to an amputation socket and provide an artificial leg and foot for the wearer.

2. The Present State of the Art

The present invention was developed to fill a need for lower limb amputee athletes who desire a foot prosthesis for specific athletic events such as track and field.

Most lower limb amputee athletes competing in track and field events must use standard prosthetic devices available commercially. There has been limited effort to custom fabricate prostheses for specific athletic events and to match the design characteristics of a particular individual.

The problem with most state-of-the-art prostheses is that they incorporate a heel which is not needed for a sprinter who runs on the ball of the foot and whose heel never contacts the ground while sprinting. Also reducing the efficiency of the foot is the foam cosmetic cover included in most commercial prostheses which adds weight and interferes with the flexing characteristics of the device. The cosmesis serves no beneficial purpose for a competitive athlete.

Another detrimental characteristic of most modern prosthetic feet is the rigid ankle joint resulting from a tubular connector which connects the foot to the stump socket. With an inflexible ankle joint, the athlete cannot expect to compete at the same level as able-bodied athletes. Two dynamic feet that are commercially available which do not have rigid ankle joints are the Springlite system and the Flex-Foot system. However both systems embody a heel segment secured to the main body of the foot either at the ankle or at the forefoot. While these systems provide better performance to the amputee track athlete than the former prostheses, these systems embrace componentry and joints which are less than optimum for sprinting competition.

There remains a need to provide a more satisfactory solution for lower limb amputee athletes who desire a foot prosthesis for specific athletic events such as track and field.

SUMMARY OF INVENTION

The present invention seeks to resolve a number of the problems which have been experienced in the prior art, as identified above. More specifically, the apparatus and method of this invention constitute an important advance in the art of foot and leg prostheses for lower limb amputee athletes, as evidenced by the following objects and advantages realized by the invention over the prior art.

One object of the present invention is to be of unitary construction.

A further object of the present invention is to eliminate a heel section which reduces the efficiency of the prosthesis.

Additionally, it is an object of the present invention to have only the toe section of the foot contact the ground while sprinting.

Yet another object of the present invention is to increase the ease in which an athlete's body rotates about the pivot point created by the toe placement.

A further object of the present invention is to prevent delamination in the ankle region.

Additional objects and advantages of the invention will be apparent from the description which follows, or may be learned by the practice of the invention.

Briefly summarized, the foregoing objects are achieved by an apparatus which comprises a shank strut section, an ankle section, a forefoot section, and a toe section, all of which are combined in a single, fiber reinforced composite lamination. The shank strut section attaches to a standard stump socket via a metal adaptor fitting or by laminating the pylon directly to the socket.

The present invention eliminates the heel section found in dynamic prosthetic feet available commercially by means of a multiple-curved ankle section which transitions into an angled forefoot section. Thus, only the toe section of the prosthesis contacts the surface during use. This feature also increases the ease at which an athlete's body rotates about the pivot point created by the toe placement.

The thickness of the ankle region is greater than the shank strut section in order to prevent delamination of the fiberglass or composite materials in the ankle region.

BRIEF DESCRIPTION OF DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the presently preferred embodiments and the presently understood best mode of the invention will be described with additional detail through use of the accompanying drawings in which.

DESCRIPTION OF THE PREFERRED EMBODIMENT

Figure 3:
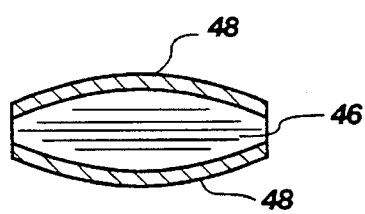
FIG. 3, is a horizontal section taken on the line 3—3 of FIG. 2.
Figure 2:
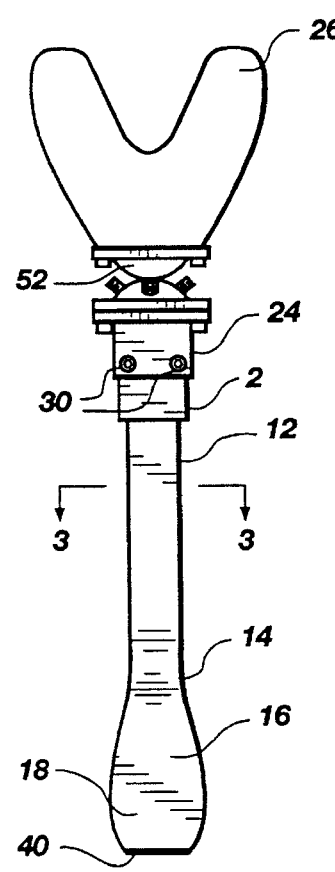
FIG. 2 is a front view of the prosthesis shown in FIG. 1.
Figure 4:
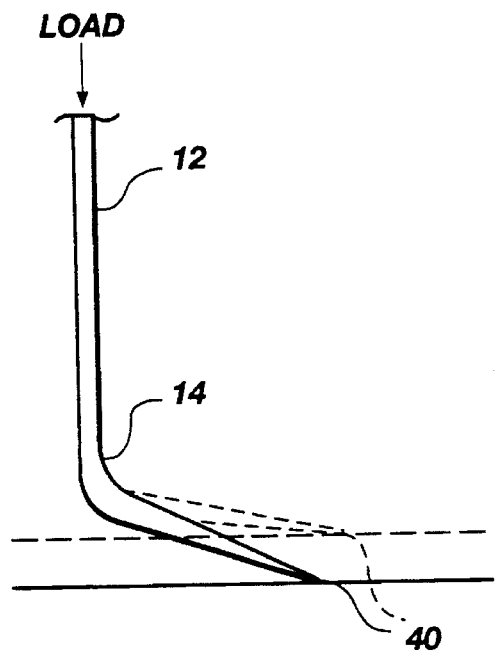
FIG. 4, a perspective view of the prosthetic foot in FIG. 1 showing the idealized deflection of the foot under full load application as occurs with a runners body weight under full stride. In phantom view, is a superimposed foot without any load application.
Figure 5:
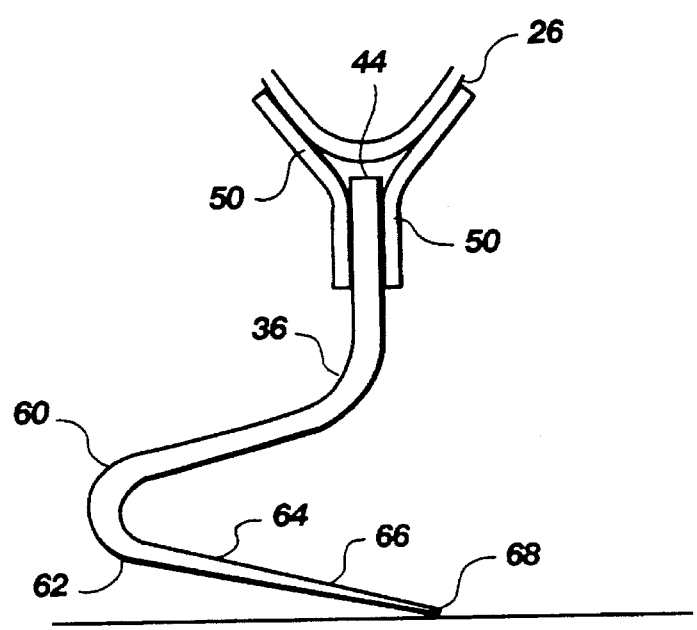
FIG. 5, is a perspective view of an alternate configuration showing a change in toe section location relative to the shank.
Figure 6:
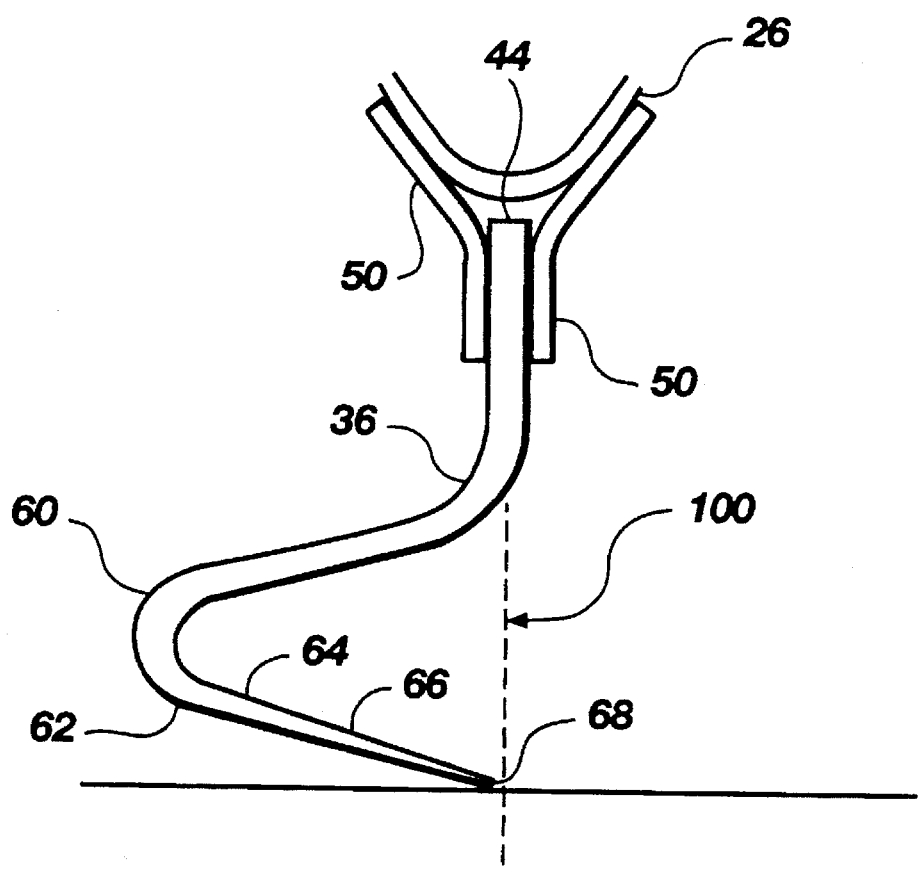
FIG. 6 is a perspective view of an alternate configuration showing the toe section located behind the vertical plane 100 defined by the shank strut section.

In the form illustrated, the foot and leg prosthesis 10 comprises an elongated shank 12, a curved ankle section 14, which changes the vertical shank strut section 12 into a forwardly extending forefoot section 16 (depicted as 64 in FIG. 5 and FIG. 6). The shank strut section 12 is of square or rectangular cross-section and can also be curved to create an optional truncated elliptical cross-section as shown in FIG. 3. The length of the shank strut section 12 varies as necessary for connection to the distal end 34 of the stump socket 26. Since the entire prosthesis 10 deflects, the length of the shank strut section 12 effects the stiffness characteristics of the system, i.e., shortening the shank strut section 12 stiffens the prosthesis 10. The ankle section 14 (60 in FIG. 5 and FIG. 6) of the prosthesis 10, defined at the upper limit 36 where the shank strut section 12 initiates a curve either forwardly or rearwardly. The upper limit 36 is also defined as the "tangent point". The lower limit 38 (depicted as 62 in FIG. 5 and FIG. 6) of the ankle section 14 (60 in FIG. 5 and FIG. 6) is the point at which the ankle section 14 (60 in FIG. 5 and FIG. 6) curves forwardly into a straight or slightly curved forefoot section 16 (64 in FIG. 5 and FIG. 6).

Figure 1:
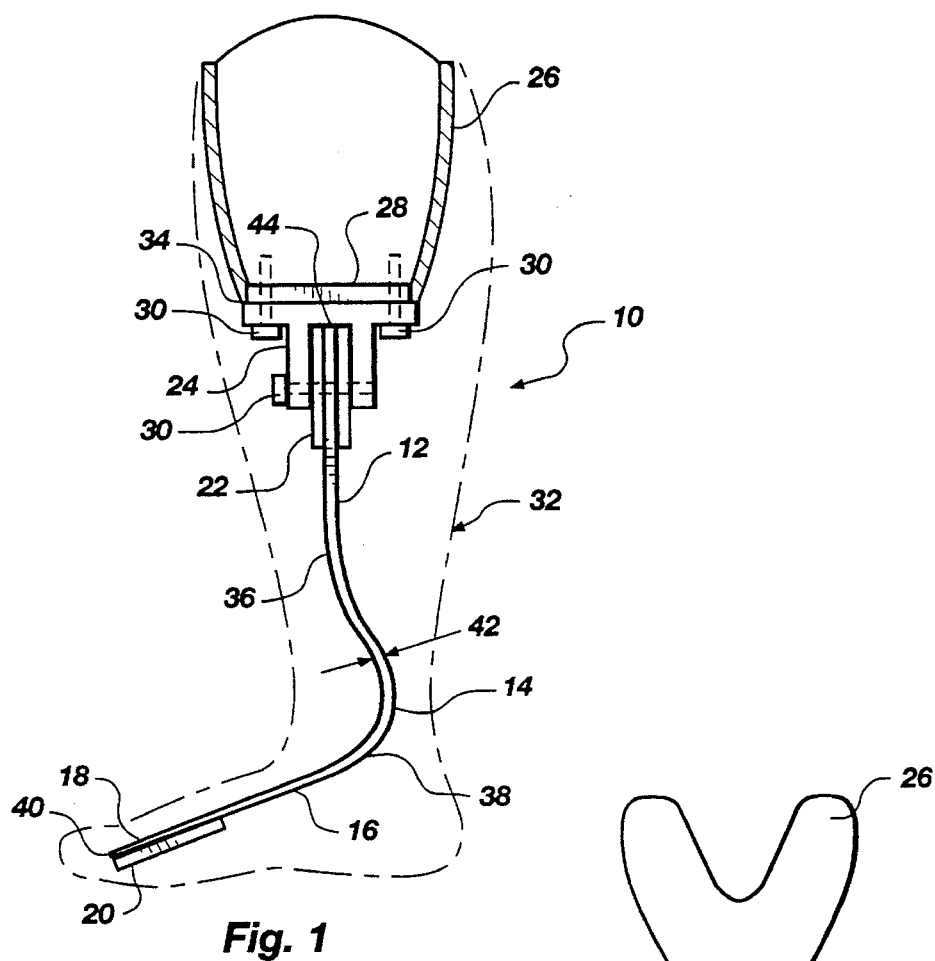
FIG. 1 is a side view in vertical section taken through an assembled foot and leg prosthesis of the invention.

The ankle section 14 (60 in FIG. 5 and FIG. 6) may curve directly forward with a single curve or it may incorporate multiple curves to complete the transition. In FIG. 1, the ankle section 14 (60 in FIG. 5 and FIG. 6) extends rearwardly at the upper limit 36 and then curves forwardly at the lower limit 38 (62 in FIG. 5 and FIG. 6). The purpose for the double curve is to create an overlength forefoot section 16 (64 in FIG. 5 and FIG. 6) with the toe tip 40 (depicted as 68 in FIG. 5 and FIG. 6) at or near the vertical plane of the shank strut section 12 which is best seen in FIG. 5. The lamination thickness 42, is greatest in the ankle section 14, in order to prevent flexing. The highest stresses exist in the ankle section 14 (60 in FIG. 5 and FIG. 6) due to the radical changes in geometry. Immobilizing the ankle section 14 (60 in FIG. 5 and FIG. 6) thus prevents delamination failures from occurring.

The materials used for construction of the foot and leg prosthesis 10 are of conventional composite laminating materials which include and are not limited to fiberglass, aramid or carbon fiber reinforcement, and epoxy or similar structural resin matrix. For design efficiency, the majority of the continuous fibers run the length of the structure from the top 44 of the shank strut section 12, through the ankle section 14 and to the toe tip 40 (68 in FIG. 5 and FIG. 6). This orientation is denoted in FIG. 3 as "0-degrees orientation" 46. Continuous cross-plied filaments 48, diagonal to the length of the prosthesis 10, add torsional integrity to the prosthesis 10 and prevent splitting of the axial filaments comprising the majority of the construction. The lamination is completed in a single process by laying up the plies onto a rigid mold shaped to the final configuration and curing with a vacuum bagged/autoclave cure process.

The composite material used in construction of the prosthesis is created by laying the unidirectional continuous fibers and/or the cross-plied fabrics in the resin matrix. The resin matrix includes epoxies, polyester, and acrylics, or combinations thereof.

The coupling of the top 44 of the shank strut section 12 to the amputees stump socket 26 may be accomplished by one of two primary means. For one method, the shank strut section 12 is positioned at the desired orientation relative to the stump socket 26, and then wet laminating materials 50, comprised of reinforcing fabric or cloth with a wet resin matrix, are draped over the joint and allowed to cure to a rigid consistency by application of heat and vacuum. This method is advantageous for keeping the added weight to a minimum. Also, the cost of materials and labor is small.

Another method involves first coating the upper end of the shank strut section 12 with an elastomer 22, such as polyurethane, and then squeezing the elastomer 22 in a mold as it cures. A machined or molded adapter fitting 24, is then slid snugly over the elastomer 22 and tightened with fasteners, 30. This adapter fitting 24 incorporates holes for subsequent fastening of the prosthesis 10 directly to a plate 28 affixed to the amputees stump socket 26 or to a permanently affixed alignment tool 52, commercially available. This system allows for quick replacement and rigid securement of components. It also allows for the use of existing alignment tools 52 to expedite adjustment of the prosthesis 10 to an optimum alignment for the amputee's needs. The primary drawback to an alignment tool 52 is the added weight and cost.

The one piece foot and leg prosthesis 10 (keel) does not have a heel component as depicted, although one could be added for non-sprinting applications. The preferred forefoot section 16 (64 in FIG. 5 and FIG. 6) is symmetric for either left or right foot applications. This is of particular importance for maintaining balance since the point of load application is the toe tip 40 (68 in FIG. 5 and FIG. 6). It is not necessary to wear a cosmetic cover 32, although an elastomeric pad 20, is desired under the forefoot section 16 (64 in FIG. 5 and FIG. 6) to prevent slipping on slick surfaces. Athletic shoes or running spikes can be used with the prosthesis 10 to increase traction and/or to comply with rules governing competition. If required, the athletic shoe can be slipped over the forefoot and ankle sections 16 (64 in FIG. 5 and FIG. 6) and 14 (60 in FIG. 5 and FIG. 6) of the prosthesis 10, which are then filled with flexible foam before lacing the shoe tight.

The configuration of the forefoot section 16 (64 in FIG. 5 and FIG. 6) is critical to the optimum performance of the prosthesis 10 in a foot race. The design variables of the prosthesis 10 include: (1) the position of the toe section 18 (depicted as 66 in FIG.5 and FIG. 6) relative to the vertical plane of the shank strut section 12; (2) the length of forefoot section 16 (64 in FIG. 5 and FIG. 6); (3) the plantar-flexion angle (the angle of the forefoot section 16 relative to the horizontal plane); and (4) the lamination layup or ply distribution of the prosthesis 10 affecting the stiffness along the length of the prosthesis 10.

The position of the toe section 18 (66 in FIG. 5 and FIG. 6) relative to the vertical plane of the shank strut section 12 has a substantial effect on the behavior of the prosthesis 10 as an athlete accelerates out of starter blocks at the beginning of a sprint. If the forefoot section 16 (64 in FIG. 5 and FIG. 6) lies in front of the vertical plane of the shank strut section 12, the sprinter experiences a resistance upon initial toe contact with the track. This will continue to occur until the body rises to a more upright position from the initial sprinter's crouch. The cause for this phenomenon is due to the horizontally moving body creating a vertical force of accelerating body mass which is resisted upon toe contact by the deflecting toe section 18 (66 in FIG. 5 and FIG. 6) of the prosthesis 10. As the toe section 18 (66 in FIG. 5 and FIG. 6) absorbs this force by the deflection of the forefoot section 16 (64 in FIG. 5 and FIG. 6) "spring," the efficient composite laminate returns this energy as the body rotates over the prosthesis 10 and completes the "toe-off" phase of the running gait. A long toe section 18 (66 in FIG. 5 and FIG. 6) wherein the prosthesis 10 contacts the ground from a lower angle prevents the toe section 18 (66 in FIG. 5 and FIG. 6) from deflecting and thus performing efficiently as intended. A toe tip 40 (68 in FIG. 5 and FIG. 6) closer to, or behind, the plane of the shank strut section 12 (see FIG. 6), is preferable for facilitating the rotation of an athlete's body about the pivot point created by the toe section 18 (66 in FIG. 5 and FIG. 6) placement.

The length of the forefoot section 16 (64 in FIG. 5 and FIG. 6) is critical in optimizing the performance of the prosthesis 10. A short forefoot section 16 (64 in FIG. 5 and FIG. 6) can deflect only slightly without risking interlaminar shear failure of the composite lamination. A longer forefoot section 16 (64 in FIG. 5 and FIG. 6), relative to a viable foot, still performs poorly in comparison to a natural foot because the spring action does not perform as well as the musculoskeletal natural limb. The present invention incorporates a forefoot section 16 (64 in FIG. 5 and FIG. 6) which is extremely long by normal foot standards to overcome these shortcomings. This lengthened forefoot section 16 (64 in FIG. 5 and FIG. 6) can store and return much greater amounts of propulsion energy than shorter versions.

A large plantar-flexion angle is also important in assuring optimum energy return. This assures that the toe section 18 (66 in FIG. 5 and FIG. 6) is always the first and only point of contact even when rising out of starter blocks at the beginning of a race. However, a sprinter must walk on his "toe tips" 40 (68 in FIG. 5 and FIG. 6) while preparing for a race. Also, decelerating after completing a sprint is accomplished by pushing against the toe tips 40 (68 in FIG. 5 and FIG. 6).

The lay-up of plies throughout the forefoot section 16 substantially affects the performance characteristics of the prosthesis 10. Initially, an athlete will experience difficulty maintaining balance on the prosthesis 10. To compensate for this imbalance, the initial device worn is made with a soft toe section 18 (66 in FIG. 5 and FIG. 6) that flexes so that a sufficient surface area of support exists while standing. As the athlete becomes acclimated to the feet, the toe section 18 (66 in FIG. 5 and FIG. 6) stiffness is increased by the extension of plies of composite laminating materials to the toe tip 40 (68 in FIG. 5 and FIG. 6). The spring stiffness and performance efficiency are increased accordingly. The optimum design exists when the entire forefoot section 16 (64 in FIG. 5 and FIG. 6) flexes uniformly without a sudden change in stiffness along its length. The toe section 18 (66 in FIG. 5 and FIG. 6) should be soft and gradually increase in stiffness to a very stiff and inflexible beam at the back or posterior end of the forefoot section, where the beam extends into the upwardly curving ankle section 14 (60 in FIG. 5 and FIG. 6).

In summary, the method and apparatus disclosed herein is a significant improvement from the present state of the art of lower limb prosthesis for amputee athletes participating in track and field.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A foot and leg prosthesis for use by an amputee having a natural limb forefoot length comprising an elongated monolithic composite member having a semi-flexible shank strut section, an arcuate ankle section, a forefoot section, and a toe section; one end of said shank strut section being connected to a socket adapted to receive an amputated leg stump, the other end extending straight to said ankle section, said member beginning said ankle section by smoothly curving rearwardly from the straightly extended portion of the shank strut section and then forwardly through said ankle section, said forefoot section and said toe section.

2. A foot and leg prosthesis as defined in claim 1, wherein said semi-flexible shank strut section is of rectangular cross-section.

3. A foot and leg prosthesis as defined in claim 1, wherein said semi-flexible shank strut section is of truncated elliptical cross-section.

4. A foot and leg prosthesis as defined in claim 1, wherein the ankle section includes a curved portion changing the direction of the member from substantially vertical at the shank strut section to substantially diagonal at the toe section.

5. A foot and leg prosthesis as defined in claim 1, wherein the member is constructed of fiberglass composite.

6. A foot and leg prosthesis as defined in claim 1, wherein the member is constructed of carbon fiber composite materials.

7. A foot and leg prosthesis as defined in claim 1, wherein the thickness of the ankle section is increased relative to the shank strut and forefoot sections to resist deflection and delamination of the composite member.

8. A foot and leg prosthesis as defined in claim 1, wherein the length of the forefoot section is longer than the amputee's natural limb forefoot length.

9. A foot and leg prosthesis for use by an amputee having a natural limb forefoot length comprising an elongated monolithic composite member having a semi-flexible shank strut section, an ankle section of greater thickness than that of the shank strut and forefoot sections, a forefoot section of longer length than an amputee's natural forefoot length, and a toe section; one end of said shank strut section being connected to a socket adapted to receive an amputated leg stump, the other end smoothly curving downwardly and then forwardly of the shank strut section through the ankle section, forefoot section and to said toe section.

10. A foot and leg prosthesis as defined in claim 9, wherein the ankle section curves rearwardly from the shank strut section and then forwardly through the forefoot section to the toe section.

11. A foot and leg prosthesis as defined in claim 9, wherein the long axis of the shank strut section defines a plane and the toe section is positioned forward of said plane.

12. A foot and leg prosthesis as defined in claim 10, wherein the long axis of the shank strut section defines a plane and the toe section is positioned behind said plane.

13. A foot and leg prosthesis as defined in claim 9, wherein the forefoot section defines an angle relative to a horizontal plane such that only the toe section contacts the ground during use.

14. A foot and leg prosthesis as defined in claim 9, wherein the prosthesis stiffness increases as the length of the shank strut section increases.

15. A foot and leg prosthesis for use by an amputee having a natural limb forefoot length comprising an elongated monolithic composite member having a semi-flexible shank strut section, an ankle section of greater thickness than that of the shank strut and forefoot sections, a forefoot section of longer length than an amputee's natural forefoot length, and a toe section; one end of said shank strut section being connected to a socket adapted to receive an amputated leg stump, the other end extending straight before smoothly curving rearwardly from the straightly extended portion of the shank strut section and then forwardly through the ankle section, forefoot section and to said toe section with all sections together forming an overall length.

16. A foot and leg prosthesis as defined in claim 15, wherein the prosthesis comprises composite materials extending from the shank strut section through the ankle section, forefoot section and to the toe section.

17. A foot and leg prosthesis as defined in claim 16, wherein the composite materials include unidirectional and cross-plied fabrics embedded in a resin matrix consisting of polyester, epoxy and acrylic.

18. A foot and leg prosthesis as defined in claim 15, further comprising cross-plied filaments which are diagonal to the overall length of the elongated monolithic composite member for added torsional integrity and for preventing splitting of the composite member.

19. A foot and leg prosthesis defined in claim 15, wherein the prosthesis is symmetric for left or right foot applications.

20. A foot and leg prosthesis as defined in claim 15, wherein the anterior toe section includes an underside, said underside having a resilient pad for contacting the ground.

* * * * *